(12) United States Patent
Matsuoka

(10) Patent No.: US 12,214,128 B2
(45) Date of Patent: Feb. 4, 2025

(54) BLOOD PRESSURE MEASURING APPARATUS, METHOD AND PROGRAM FOR MEASURING BLOOD PRESSURE, AND RESPIRATION ASSISTANCE APPARATUS

(71) Applicant: OMRON HEALTHCARE CO., LTD., Muko (JP)

(72) Inventor: Yasushi Matsuoka, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 767 days.

(21) Appl. No.: 16/995,854

(22) Filed: Aug. 18, 2020

(65) Prior Publication Data

US 2020/0376217 A1 Dec. 3, 2020

Related U.S. Application Data

(63) Continuation of application No. PCT/JP2019/000839, filed on Jan. 15, 2019.

(30) Foreign Application Priority Data

Feb. 22, 2018 (JP) ................................. 2018-029889

(51) Int. Cl.
*A61B 5/021* (2006.01)
*A61B 5/00* (2006.01)
*A61M 16/00* (2006.01)

(52) U.S. Cl.
CPC .......... *A61M 16/026* (2017.08); *A61B 5/021* (2013.01); *A61B 5/4818* (2013.01);
(Continued)

(58) Field of Classification Search
CPC ............ A61M 16/026; A61M 16/0069; A61M 2210/0618; A61M 2230/30;
(Continued)

(56) References Cited

U.S. PATENT DOCUMENTS

| | | | |
|---|---|---|---|
| 7,179,229 B1 * | 2/2007 | Koh ................... | A61N 1/36114 600/483 |
| 2006/0023228 A1 * | 2/2006 | Geng ..................... | A61B 5/411 356/601 |

(Continued)

FOREIGN PATENT DOCUMENTS

| | | |
|---|---|---|
| JP | 64-27535 A | 1/1989 |
| JP | 2006-212218 A | 8/2006 |

(Continued)

OTHER PUBLICATIONS

English translation of Official Communication issued in International Patent Application No. PCT/JP2019/000839, mailed on Sep. 3, 2020 and Apr. 9, 2019.

(Continued)

*Primary Examiner* — Andrey Shostak
(74) *Attorney, Agent, or Firm* — Keating & Bennett, LLP

(57) ABSTRACT

According to one embodiment, a blood pressure measuring apparatus includes a blood pressure measurement unit, a warning estimator, and a signal output unit. The measurement unit measures blood pressure of a target person. The estimator monitors variation of blood pressure measured by the measurement unit and estimates the variation of the blood pressure as a sign of a blood pressure increase associated with an onset of sleep apnea syndrome if the blood pressure continuously decreases to a preset threshold or lower for a predetermined time or longer. The output unit outputs a sign notification signal to outside of the apparatus if the sign is estimated by the estimator.

5 Claims, 7 Drawing Sheets

(52) U.S. Cl.
CPC .......... *A61B 5/4836* (2013.01); *A61B 5/7282* (2013.01); *A61B 5/746* (2013.01); *A61M 16/0069* (2014.02); *A61M 2210/0618* (2013.01); *A61M 2230/30* (2013.01)

(58) Field of Classification Search
CPC ............ A61M 16/0666; A61M 16/161; A61M 2205/07; A61M 2205/3306; A61M 2205/3317; A61M 2205/332; A61M 2205/3334; A61M 2205/3358; A61M 2205/3368; A61M 2205/3375; A61M 2205/3592; A61M 2205/42; A61M 2205/505; A61M 2205/52; A61M 2209/088; A61M 2230/63; A61M 2205/8212; A61B 5/021; A61B 5/4818; A61B 5/4836; A61B 5/7282; A61B 5/746; A61B 5/022; G16H 20/40; G16H 40/60

See application file for complete search history.

(56) References Cited

U.S. PATENT DOCUMENTS

| | | |
|---|---|---|
| 2006/0200011 A1 | 9/2006 | Suzuki et al. |
| 2010/0081943 A1* | 4/2010 | Watson ................ A61B 5/4809 600/484 |
| 2011/0046498 A1 | 2/2011 | Klap et al. |
| 2011/0112442 A1 | 5/2011 | Meger et al. |
| 2015/0267695 A1 | 9/2015 | Marsh |
| 2017/0281076 A1 | 10/2017 | Takahashi et al. |
| 2019/0090818 A1 | 3/2019 | Nakajima et al. |

FOREIGN PATENT DOCUMENTS

| | | |
|---|---|---|
| JP | 2012-502671 A | 2/2012 |
| WO | 2016/035460 A1 | 3/2016 |
| WO | 2017/179698 A1 | 10/2017 |

OTHER PUBLICATIONS

Official Communication issued in International Patent Application No. PCT/JP2019/000839, mailed on Apr. 9, 2019.

* cited by examiner

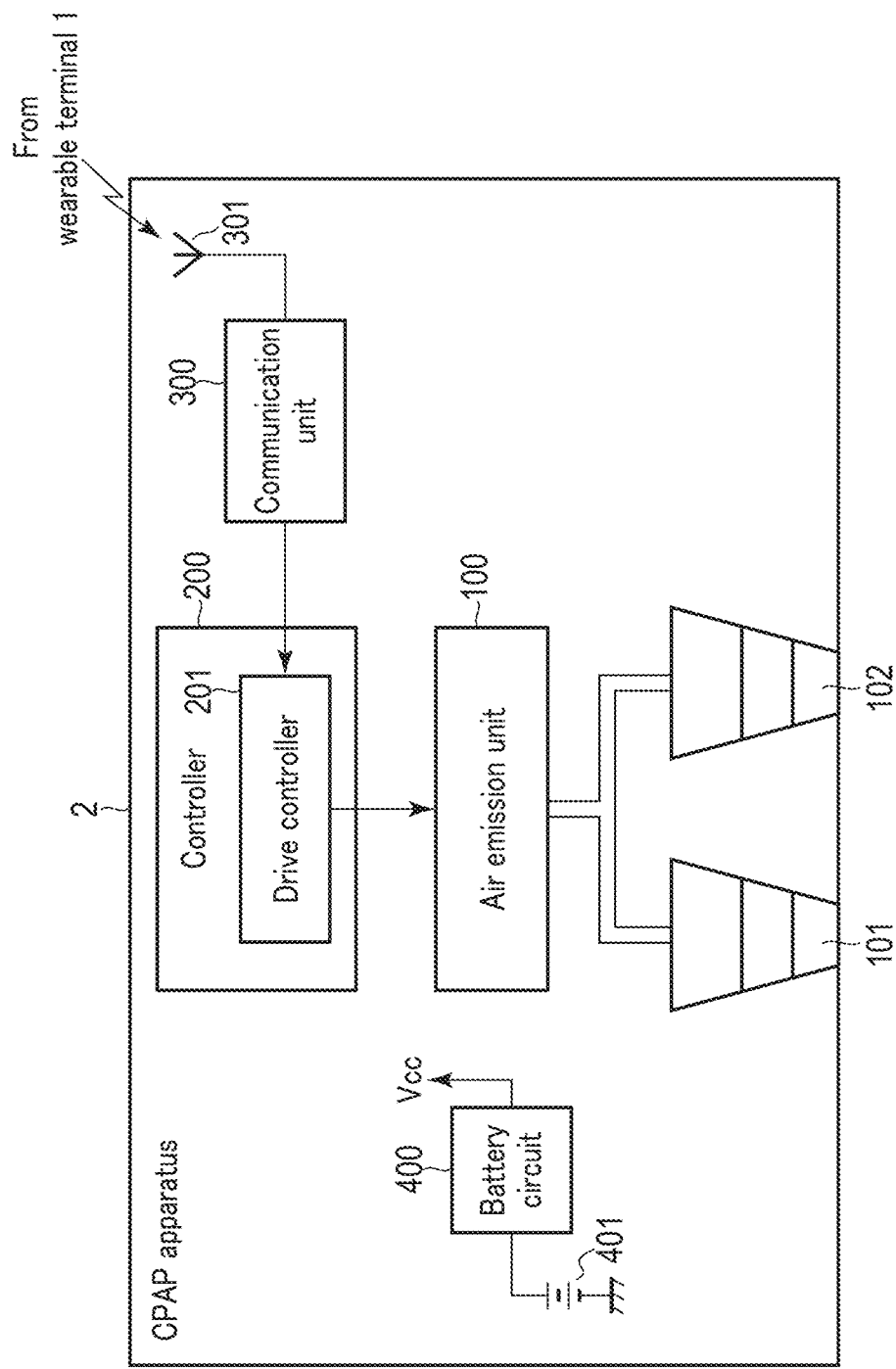
F I G. 3

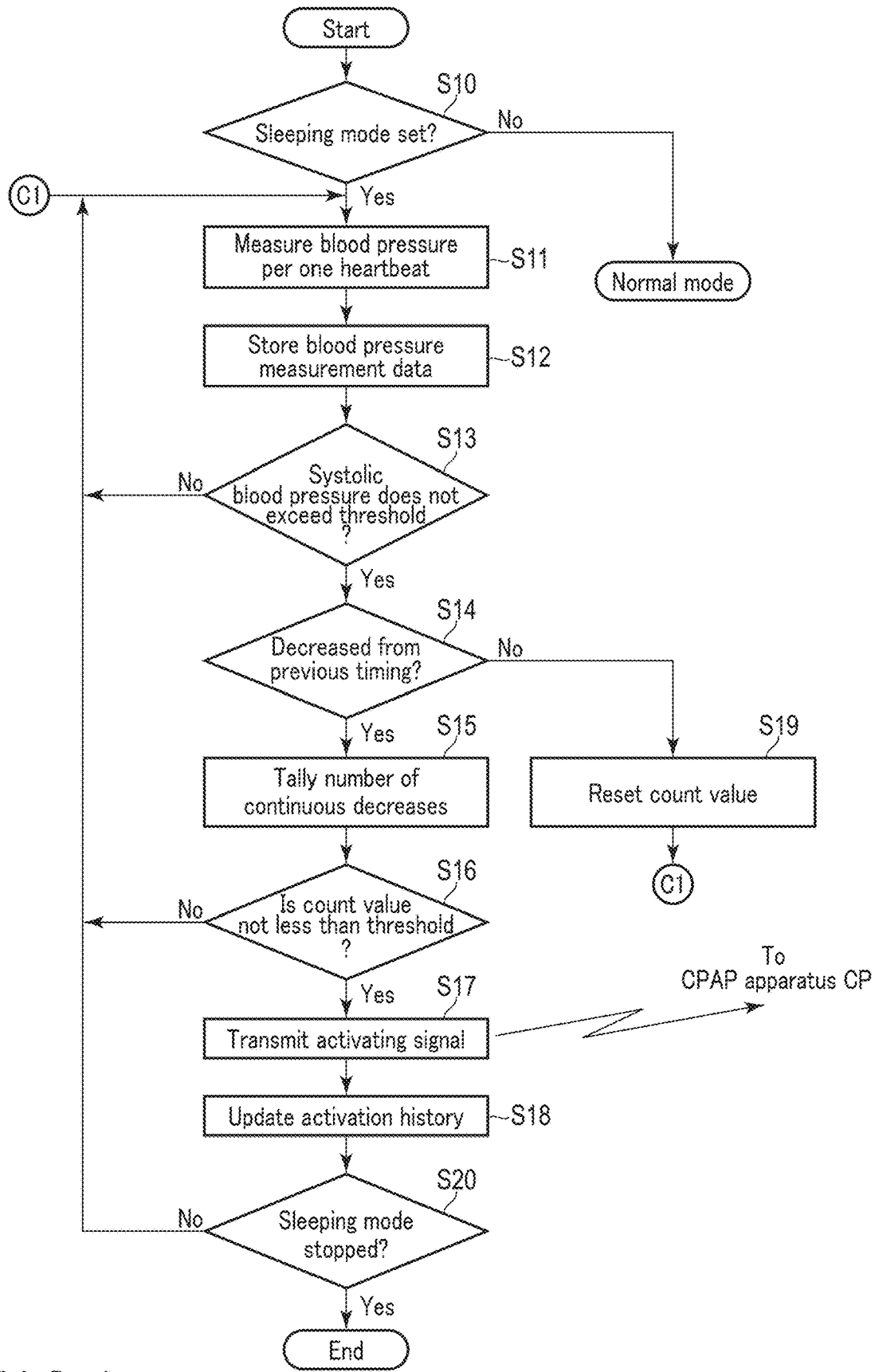
F I G. 4

BLOOD PRESSURE MEASURING APPARATUS, METHOD AND PROGRAM FOR MEASURING BLOOD PRESSURE, AND RESPIRATION ASSISTANCE APPARATUS

CROSS-REFERENCE TO RELATED APPLICATIONS

This application is a Continuation Application of PCT Application No. PCT/JP2019/000839, filed Jan. 15, 2019 and based upon and claiming the benefit of priority from Japanese Patent Application No. 2018-029889, filed Feb. 22, 2018, the entire contents of all of which are incorporated herein by reference.

FIELD

One aspect of the present embodiments relates to, for example, a blood pressure measuring apparatus for measuring blood pressure of a target person, a method and a program for measuring blood pressure, and a respiration assistance apparatus used together with the blood pressure measuring apparatus.

BACKGROUND

A disease that leads to respiratory arrest or hypopnea during sleep is known. This disease is called sleep apnea syndrome (SAS). Sleep apnea syndrome is very undesirable, firstly, because it causes repeated arousal of consciousness during sleep and resulting symptoms, such as brain insomnia and intolerable daytime sleepiness; and secondly, because, should the symptoms worsen, it will lead to an increase in the risk of both accidents while driving and development of heart and lifestyle-related diseases.

For example, continuous positive airway pressure (CPAP) is known as a countermeasure against sleep apnea syndrome. An apparatus for performing CPAP (hereinafter referred to as a "CPAP apparatus") is an apparatus for preventing airway constriction during inhalation by, for example, applying a mask to the nose of a user and sending pressurized positive pressure air from a nasal sieve apparatus to the mask, via a tube, to expand soft tissue around the tongue base. There is also known a small micropump-type apparatus in which a battery-driven pump and an air supply unit are integrated, which is attached to the nasal cavity to supply positive pressure air. The micropump-type apparatus has the advantage of obviating the need for a mask, a tube, a power supply cord, and the like, thus imposing only a small burden upon the user (see, for example, U.S. Patent Application Publication No. 2015/267695).

SUMMARY

A first aspect of a blood pressure measuring apparatus of the present embodiments is such that the blood pressure measuring apparatus includes: a blood pressure measurement unit configured to measure blood pressure of a target person; a warning estimator configured to: monitor variation of blood pressure measured by the blood pressure measurement unit; and estimate the variation of the blood pressure as a sign of a blood pressure increase associated with an onset of sleep apnea syndrome if the blood pressure continuously decreases to a preset threshold or lower for a predetermined time or longer; and a signal output unit configured to output a sign signal to outside of the apparatus when the sign is estimated by the warning estimator.

According to the first aspect of the blood pressure measuring apparatus of the present embodiments, when the blood pressure of the target person continuously decreases to a preset threshold or lower for a predetermined time or longer, the variation of the blood pressure is estimated as a sign of a blood pressure increase associated with an onset of sleep apnea syndrome, and a sign notification signal is output to outside of the apparatus.

Therefore, when the respiration assistance apparatus is operated using the sign notification signal as a trigger, for example, it is possible to start a respiration assistance operation of the respiration assistance apparatus for the target person before the blood pressure of the target person increases due to the influence of sleep apnea. That is, it is possible to timely perform continuous positive airway pressure as a measure against sleep apnea syndrome on the target person, and thus it is possible to suppress a blood pressure increase associated with the onset of sleep apnea syndrome, that is, suppress the occurrence of a blood pressure surge.

In addition, since it is possible to stop the air supply operation of the respiration assistance apparatus during the period until the sign notification signal is output, it is possible to reduce the power consumption of the respiration assistance apparatus as compared to the case where the air supply operation is always performed during sleep. This is extremely effective, particularly in the case of a micropump-type apparatus that uses a battery as a power source, as it becomes difficult to stop the operation during sleep and obviates the need for a large-capacity battery. In addition, since the respiration assistance apparatus can be operated only when necessary and can be set to an operation stop state in the other periods, it is possible to suppress noise of the respiration assistance apparatus in a period when the continuous positive airway pressure need not be performed, and possible to improve the quietness during sleep.

A second aspect of the blood pressure measuring apparatus of the present embodiments is such that the blood pressure measurement unit is configured to measure blood pressure of the target person per one heartbeat.

According to the second aspect of the blood pressure measuring apparatus of the present embodiments, the blood pressure of the target person is measured per one heartbeat; therefore, it is possible to almost continuously measure the blood pressure variation of the target person and, accordingly, possible to reliably estimate the sign of the blood pressure increase associated with the onset of sleep apnea syndrome without missing the sign.

A third aspect of the blood pressure measuring apparatus of the present embodiments is such that the warning estimator is configured to estimate the variation of the blood pressure as a sign of a blood pressure increase accompanying an onset of sleep apnea syndrome if the measured blood pressure continuously decreases to a preset threshold or lower for a predetermined time or longer, and then starts to increase.

According to the third aspect of the blood pressure measuring apparatus of the present embodiments, when the blood pressure continuously decreases to the threshold or lower for a predetermined time or longer and then turns upward, the variation of the blood pressure at this time is estimated as a sign of the blood pressure increase accompanying the onset of sleep apnea syndrome. Therefore, it is possible to more timely and reliably estimate the sign of the blood pressure increase associated with the onset of sleep apnea syndrome.

A fourth aspect of the blood pressure measuring apparatus of the present embodiments is such that the signal output unit is configured to output, as the sign notification signal, an activating signal to a respiration assistance apparatus performing continuous positive airway pressure as a measure against the sleep apnea syndrome.

According to the fourth aspect of the blood pressure measuring apparatus of the present embodiments, the sign notification signal is directly output to the respiration assistance apparatus as an activating signal. Therefore, the respiration assistance apparatus can be automatically and reliably activated before the blood pressure of the target person increases.

A first aspect of the respiration assistance apparatus of the present embodiments is such that the respiration assistance apparatus is connected, via a signal transmission path, to the blood pressure measuring apparatus according to the third aspect described above, and that the respiration assistance apparatus includes: an apparatus main body configured to perform an operation for continuous positive airway pressure as a measure against sleep apnea syndrome for the target person; a signal reception unit configured to receive an activating signal transmitted from the blood pressure measuring apparatus via the signal transmission path; and a controller configured to stop the operation of the apparatus main body in a standby state, and start the operation of the apparatus main body in response to reception of the activating signal.

According to the first aspect of the respiration assistance apparatus of the present embodiments, the respiration assistance apparatus is set to an operation stop state in the standby state, and starts the operation in response to the activating signal from the blood pressure measuring apparatus. Therefore, power consumption is reduced as compared with a case where the respiration assistance apparatus is always operated, whereby when the respiration assistance apparatus is a battery-driven type, for example, it becomes difficult to stop the operation during sleep and obviates the need for a large-capacity battery. Also, a type of respiration assistance apparatus that uses a commercial power source as a power source can maintain quietness during a standby state by not being operated at all times.

A second aspect of the respiration assistance apparatus of the present embodiments is such that the controller is configured to stop the operation at a time point when a preset time elapses after starting the operation of the apparatus main body.

According to the second aspect of the respiration assistance apparatus of the present embodiments, the respiration assistance apparatus starts operating in response to the activating signal transmitted from the blood pressure measuring apparatus, and automatically stops operating and returns to the standby state after a predetermined time elapses. Therefore, the power consumption can be further reduced as compared with a case where the apparatus does not have an automatic function.

That is, according to each aspect of the present embodiments, it is possible to reduce power consumption and improve quietness of a respiration assistance apparatus that performs continuous positive airway pressure.

BRIEF DESCRIPTION OF THE DRAWINGS

FIG. 3 is a block diagram showing a functional configuration of a CPAP apparatus as a respiration assistance apparatus according to an embodiment.

FIG. 4 is a flowchart showing a process procedure and process content of the wearable terminal shown in FIG. 2.

DETAILED DESCRIPTION

Hereinafter, embodiments will be described with reference to the drawings.

Both the mask-type and the micropump-type CPAP apparatuses are configured to perform an air supply operation at all times during sleep, so that power consumption during sleep increases and challenges concerning quietness are also posed. In particular, in the case of a micropump-type apparatus using a battery as a power source, the increase in power consumption is very undesirable because the operation may be stopped during sleep due to consumption of the battery. Also, in order to prevent the operation from being stopped during sleep, it is necessary to prepare a battery having a large capacity, which inevitably increases the size and weight of the apparatus. On the other hand, in regard to quietness, whether the mask-type apparatus or the micropump-type apparatus is used, the pump always operates during sleeping hours to discharge air, thereby generating noise, which may interfere with sleeping of the person himself or herself and surrounding people.

The present embodiments have been made in view of the above circumstances, and an object of the present embodiments in one aspect is to provide a technique for reducing power consumption and improving quietness of a respiration assistance apparatus that performs continuous positive airway pressure.

Embodiment

Configuration

Figure 1:
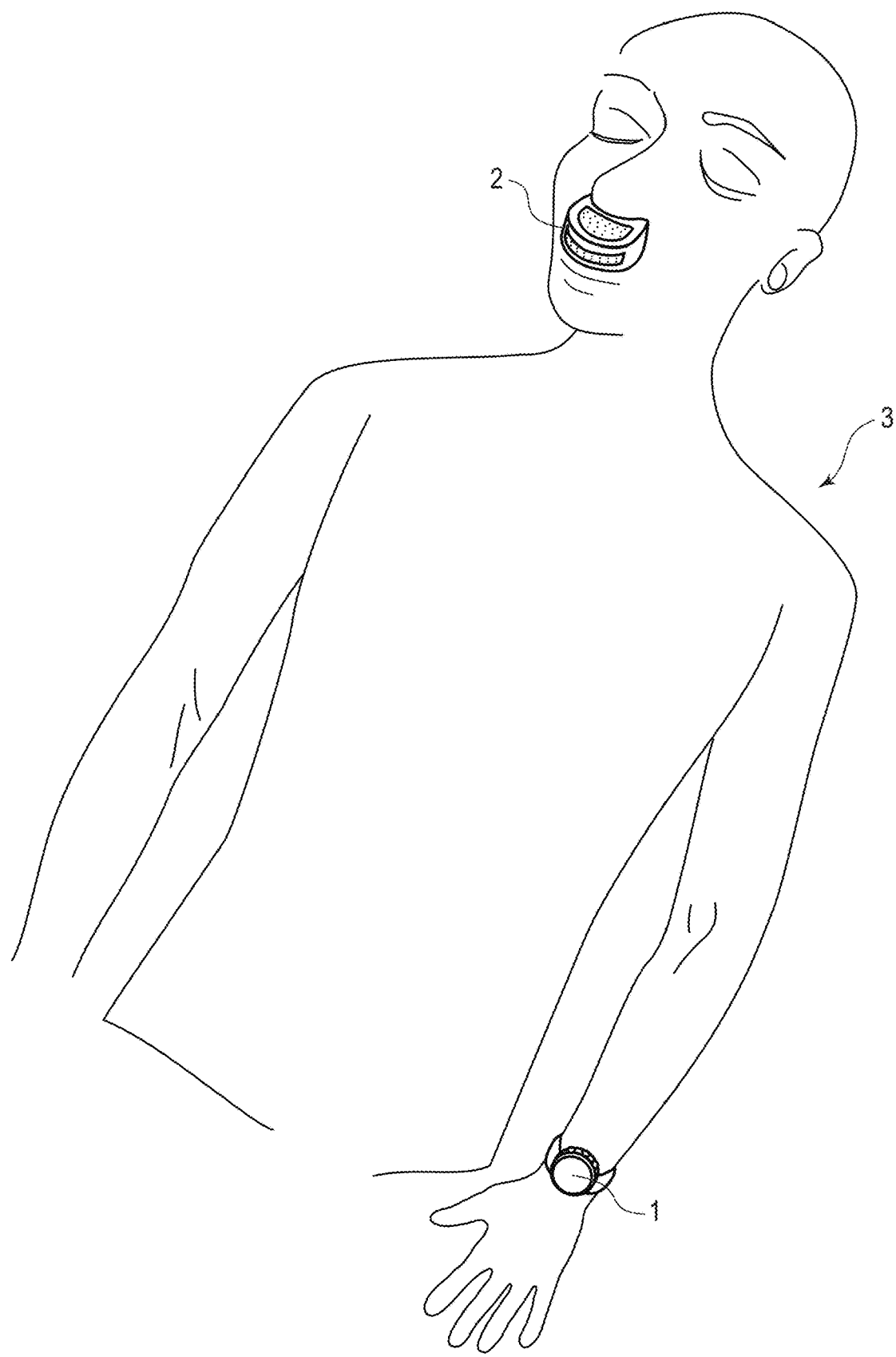
FIG. 1 is a diagram showing an example in which a blood pressure measuring apparatus and a respiration assistance apparatus according to an embodiment are attached to a target person.

FIG. 1 is a diagram showing an example in which a blood pressure measuring apparatus and a respiration assistance apparatus according to an embodiment are attached to a target person.

(1) Blood Pressure Measuring Apparatus

The blood pressure measuring apparatus is comprised of a wearable blood pressure monitor 1. The wearable blood pressure monitor 1 is worn on, for example, either one of the right or left wrist of a target person 3. The respiration assistance apparatus is a micropump-type apparatus that performs continuous positive airway pressure (CPAP), and is attached to the nostrils of the target person 3. The respiration assistance apparatus is hereinafter referred to as a "CPAP apparatus 2".

The wearable blood pressure monitor 1 has a function of periodically and automatically measuring the blood pressure of the target person 3, and adopts, for example, a beat-by-beat method of measuring the blood pressure of the target person 3 via a tonometry method per one heartbeat. As a method of continuously measuring the blood pressure, a method other than the beat-by-beat method may be adopted. For example, a trigger measurement method can be adopted. The trigger measurement method is a method of estimating blood pressure variation via a pulse transit time (PTT) method and measuring blood pressure in a spot manner using the estimated variation as a trigger. Despite not being a method for automatically measuring the blood pressure periodically, an oscillometric method using a cuff may also be adopted, as long as the measurement cycle can be set to a short timescale of, for example, several seconds (10 or less). In addition to the tonometry method, various methods such as an optical method, a radio wave method, and an ultrasonic PTT method can be adopted as a blood pressure sensing method.

Figure 2:
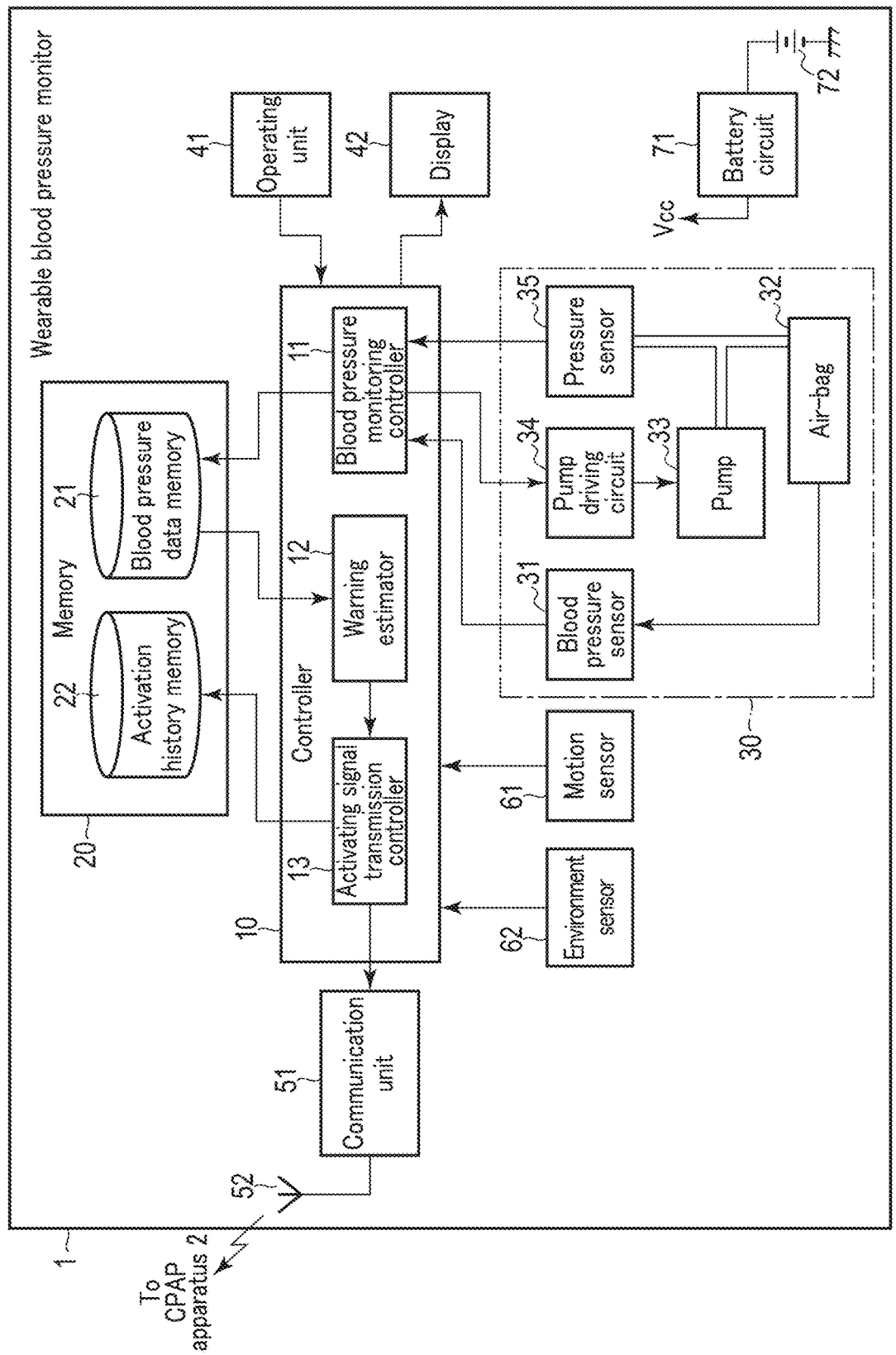
FIG. 2 is a block diagram showing a functional configuration of a wearable blood pressure monitor as a blood pressure measuring apparatus according to an embodiment.

FIG. 2 is a block diagram showing a functional configuration of the wearable blood pressure monitor 1. The wearable blood pressure monitor 1 includes a controller 10, a memory 20, and a blood pressure monitoring unit 30. The wearable blood pressure monitor 1 further includes an operating unit 41 and a display 42 used as a man-machine interface, a communication unit 51 for performing wireless communication, a motion sensor 61, an environment sensor 62, and a battery circuit 71.

The operating unit 41 and the display 42 are used by the target person 3 to designate and input an operation mode and the like, and to display a measurement result of blood pressure, an operation mode of the blood pressure monitor, and the like. The communication unit 51 includes an antenna 52 and is used to wirelessly transmit data to, and receive data from, an external apparatus. As the communication protocol, a protocol based on a low-power wireless data communication standard, such as Bluetooth Low Energy (BLE) (registered trademark), is used. The battery circuit 71 generates a power supply voltage Vcc for operating each unit of the blood pressure monitor based on the output voltage of a battery 72, and supplies the power supply voltage Vcc to each unit in the blood pressure monitor 1.

The motion sensor 61 is used to detect a body motion of the target person 3, and for example, a three-axis acceleration sensor or a three-axis angular velocity sensor is used. Based on the data of the three-axis acceleration or the three-axis angular velocity detected by the motion sensor 61, the amount of activity and the number of steps of the target person 3 during wake-up can be calculated, and a state of turning over in bed during sleep, that is, a sleeping state, can be detected. The posture of the target person 3 at the time of blood pressure measurement can also be detected based on the data of the three-axis acceleration or the three-axis angular velocity. The environment sensor 62 measures the temperature, humidity, atmospheric pressure, and the like of the area around the target person 3, and a temperature/humidity sensor or an atmospheric pressure sensor is used.

The blood pressure monitoring unit 30 includes a blood pressure sensor 31, an air-bag 32, a pump 33, a pump driving circuit 34, and a pressure sensor 35. The blood pressure sensor 31 measures the blood pressure of the target person 3 via the tonometry method per one heartbeat. The air-bag 32, the pump 33, the pump driving circuit 34, and the pressure sensor 35 are used to press the blood pressure sensor 31 against the skin, on the radial artery of the wrist of the target person 3 with a predetermined pressure, in order to accurately perform blood pressure measurement via the tonometry method.

The memory 20 uses, as a storage medium, a nonvolatile memory such as a solid state drive (SSD) that allows for write and read at any time, and a volatile memory such as a random access memory (RAM) that allows for write and read at any time, and includes a blood pressure data memory 21 and an activation history memory 22 as memories necessary for implementing an embodiment.

The blood pressure data memory 21 stores, in time series with a time stamp, data of the blood pressure of the target person 3 measured by the blood pressure monitoring unit 30. The time stamp is generated by a clock circuit (not shown). The activation history memory 22 is used to store the estimation result of the sign of the blood pressure surge or information indicating the activation history of the CPAP apparatus 2.

The controller 10 includes a hardware processor and a working memory, and includes a blood pressure monitoring controller 11, a warning estimator 12, and an activating signal transmission controller 13 as processing functions necessary for implementing an embodiment. These processing functions are fulfilled by causing the hardware processor to execute a program stored in a program memory of the memory 20.

The blood pressure monitoring controller 11 drives the pump 33 to inject air into the air-bag 32 by controlling the pump driving circuit 34 according to the pressure of the air-bag 32 detected by the pressure sensor 35. As a result, the blood pressure sensor 31 is pressed, by the air-bag 32, against the skin on the radial artery of the wrist of the target person 3 with a predetermined pressure. Then, in this state, the blood pressure monitoring controller 11 samples a blood pressure value measured by the blood pressure sensor 31 per one heartbeat, and stores the blood pressure data in the blood pressure data memory 21 with a time stamp attached thereto.

The warning estimator 12 performs a process of estimating a sign of a blood pressure surge accompanying the onset of sleep apnea syndrome based on the blood pressure data stored in the blood pressure data memory 21. Specifically, every time the blood pressure data for the most recent heartbeat is stored in the blood pressure data memory 21, the blood pressure data is read. It is then determined whether or not the systolic blood pressure represented by the blood pressure data for the most recent heartbeat is equal to or lower than a preset threshold. If the result of the determination shows that the systolic blood pressure is equal to or lower than the threshold, it is determined whether or not the systolic blood pressure measured thereafter continuously shows a tendency to decrease for a time corresponding to a predetermined heart rate. If the decrease in the systolic blood pressure continues for the aforementioned heart rate, the decrease in the systolic blood pressure is estimated as a sign of a blood pressure surge accompanying the onset of sleep apnea syndrome.

If the sign of the blood pressure surge is estimated by the warning estimator 12, the activating signal transmission controller 13 performs a process of outputting an activating signal for activating the CPAP apparatus 2 to the communication unit 51 and then transmitting the activating signal from the communication unit 51 to the CPAP apparatus 2.

(2) Respiration Assistance Apparatus

Next, the CPAP apparatus 2 as a respiration assistance apparatus is configured as described below. FIG. 3 is a block diagram showing a functional configuration thereof.

Specifically, the CPAP apparatus 2 includes an air emission unit 100, emission holes 101 and 102, a controller 200, a communication unit 300, and a battery circuit 400.

The air emission unit 100 is provided with, for example, a small fan, and emits air with the fan. The emission holes 101 and 102 have, for example, a tapered cylindrical shape.

The emission holes 101 and 102 increase the pressure of the air emitted from the air emission unit 100 and inject the air into both nostrils of the target person 3.

The communication unit 300 includes an antenna 301, receives and demodulates the activating signal wirelessly transmitted from the wearable blood pressure monitor 1, and inputs the activating signal to the controller 200. For example, Bluetooth Low Energy (BLE) (registered trademark) is adopted as the communication protocol, as in the case of the communication unit 51 of the wearable blood pressure monitor 1.

The controller 200 includes a processor and a memory, and also a drive controller 201 as a control function necessary for implementing an embodiment. When the power is turned on, the drive controller 201 sets the operation mode of the CPAP apparatus 2 to a standby mode. The standby mode is an operation mode in which only the controller 200 and the communication unit 300 are set to an operation state, and the air emission unit 100 is set to an operation stop state. When the activating signal is received by the communication unit 300 in the standby mode, the drive controller 201 activates the air emission unit 100 to start an operation of emitting the air. The operation of the air emission unit 100 is stopped when a preset operation continuation time has elapsed since the air emission unit 100 has been activated. The operation continuation time is set, for example, according to the maximum length of a single continuation time for apnea of the target person 3.

The battery circuit 400 generates a power supply voltage Vcc for operating each unit of the CPAP apparatus 2 based on the output voltage and current of the battery 401, and supplies the power supply voltage Vcc to each unit.

(Operation)

Next, operations of the wearable blood pressure monitor 1 and the CPAP apparatus 2 configured as described above will be described.

(1) Operation of Wearable Blood Pressure Monitor

Figure 6:
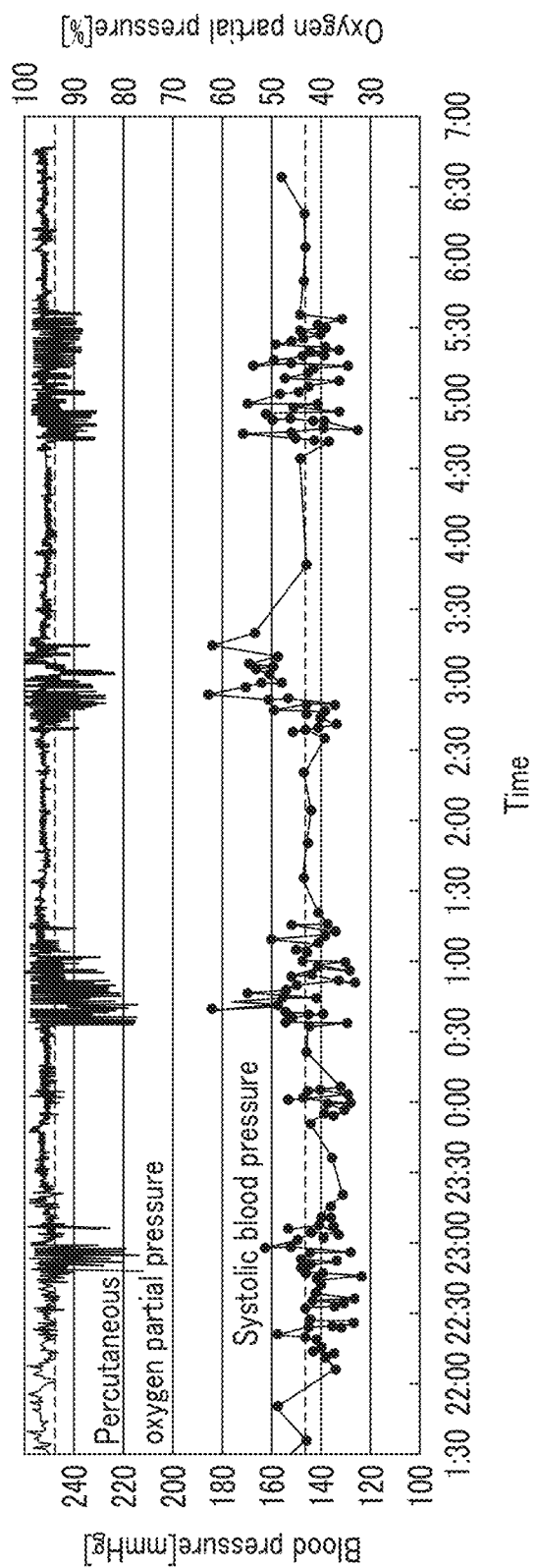
FIG. 6 is a diagram showing an example of a relationship between sleep apnea syndrome and blood pressure sleep surge occurrence.
Figure 7:
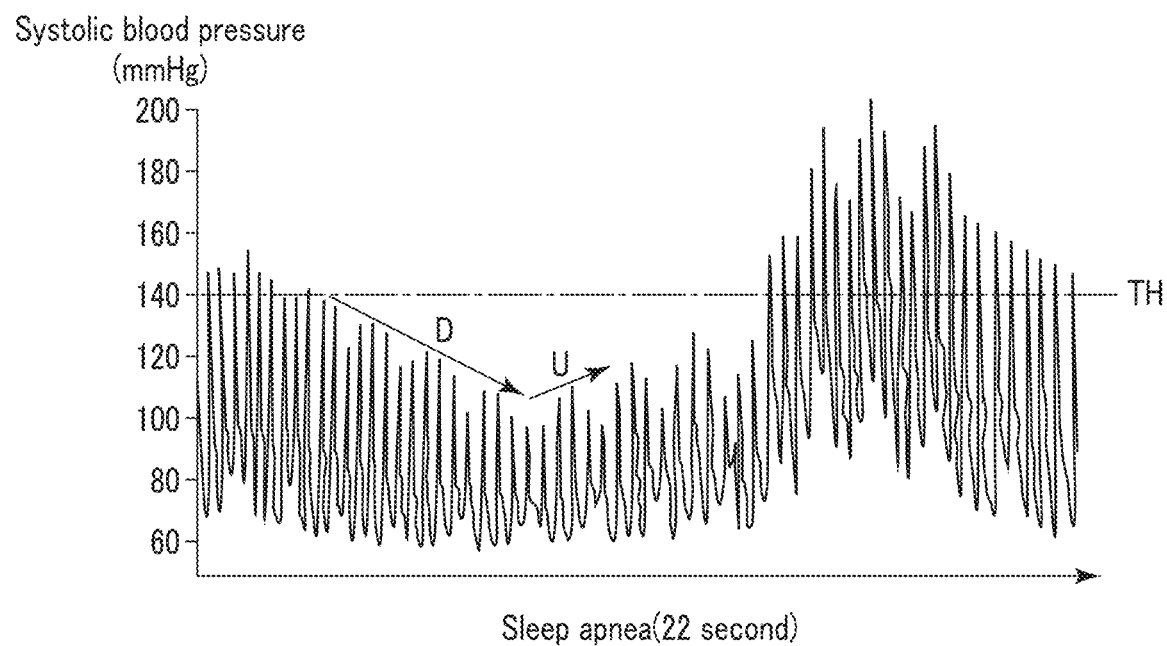
FIG. 7 is a diagram showing a typical example of a blood pressure sleep surge occurring with the onset of sleep apnea syndrome.

Sleep apnea syndrome often occurs periodically during sleep, and a significant increase in blood pressure (blood pressure surge) is caused when an apneic condition occurs. FIG. 6 is a diagram showing an example thereof, in which the upper graph shows a change in percutaneous arterial oxygen saturation (oxygen partial pressure) SpO2 [%] and the lower graph shows a change in systolic blood pressure [mmHg] in such a manner that these changes are associated with each other on a time series. FIG. 7 is an enlarged view of a manner of change in systolic blood pressure when an apneic condition occurs.

As shown in FIG. 7, in the apneic condition, the systolic blood pressure at one point falls below a value TH, lower by a certain amount than an average value of sleeping blood pressure; this decreasing tendency continues for a certain period of time as shown in D of FIG. 7; thereafter the blood pressure turns upward, as shown in U of FIG. 7, and rapidly increases in the latter period of the apneic condition to cause a blood pressure surge.

In an embodiment, the sign of the blood pressure surge is estimated as described below by focusing on the change characteristics of the systolic blood pressure associated with the occurrence of the apneic condition, thereby controlling the CPAP apparatus 2.

Figure 5:
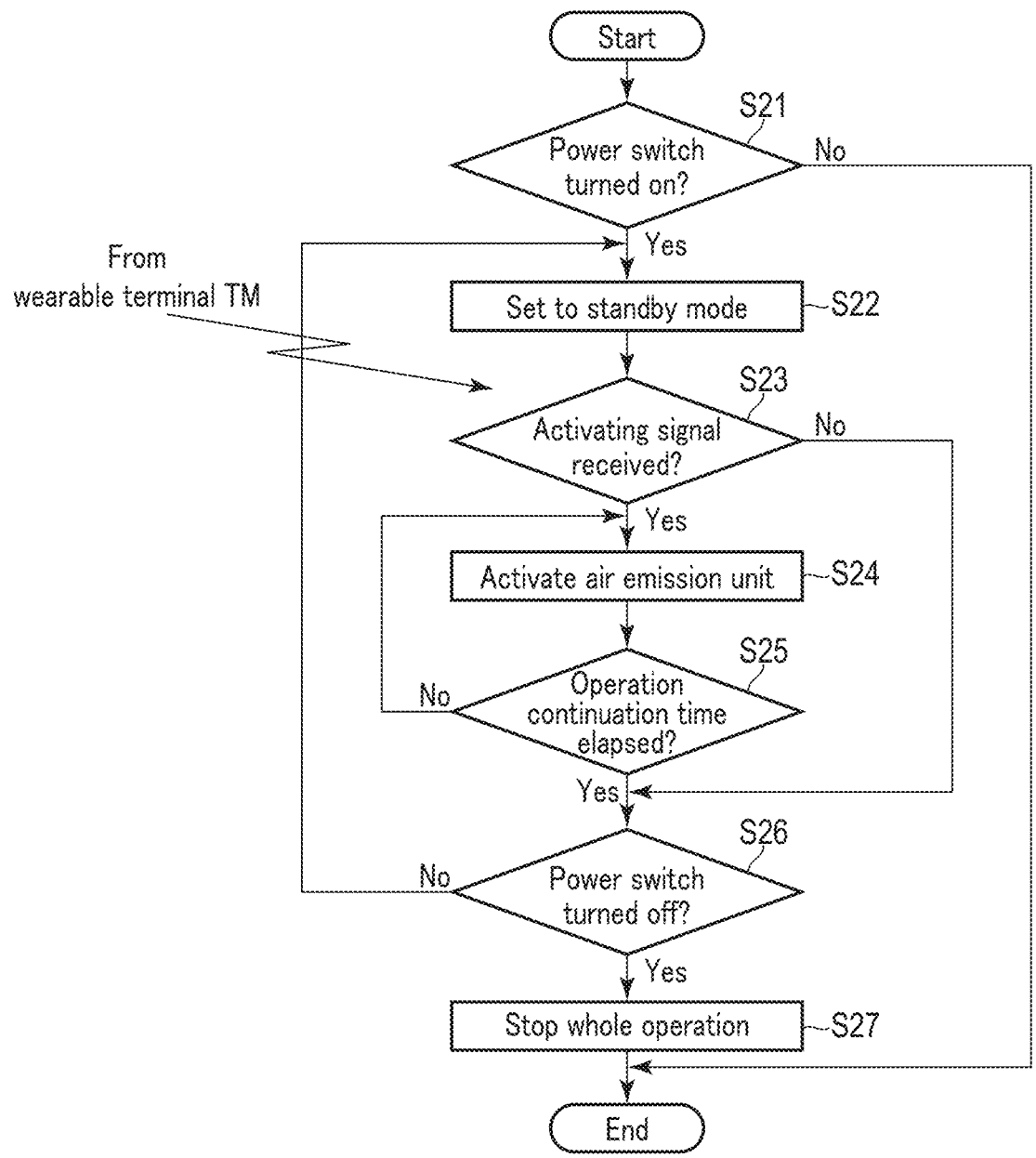
FIG. 5 is a flowchart showing a process procedure and process content of the CPAP apparatus shown in FIG. 3.

FIG. 4 is a flowchart showing a process procedure and process content of the wearable blood pressure monitor 1, and FIG. 5 is a flowchart showing a process procedure and process content of the CPAP apparatus 2.

Before going to bed, the target person 3 wears the CPAP apparatus 2 on the nostrils and performs an operation for setting an operation mode to a sleeping mode in the operating unit 41 of the wearable blood pressure monitor 1. When the wearable blood pressure monitor 1 detects the operation of setting the sleeping mode in step S10, the wearable blood pressure monitor 1 first measures the blood pressure of the target person 3 per one heartbeat in step S11 under the control of the blood pressure monitoring controller 11. Then, the blood pressure data obtained by the measurement is stored in the blood pressure data memory 21 in step S12 after the attachment of a time stamp to the data.

When the blood pressure data for the most recent heartbeat is stored in the blood pressure data memory 21, the wearable blood pressure monitor 1 reads the blood pressure data for the most recent heartbeat from the blood pressure data memory 21 in step S13, under the control of the warning estimator 12. It is then determined whether or not the systolic blood pressure included in the blood pressure data is equal to or lower than a preset threshold TH. The threshold TH is set to, for example, a value lower by a certain amount than an average value of the systolic blood pressure of sleep shown in FIG. 7. The threshold TH may be set based on a result of measurement of the sleep blood pressure for each target person 3. The threshold TH need not be set for each target person 3, and may be set to a value lower by a certain amount than a general average sleep blood pressure of a patient diagnosed with sleep apnea syndrome.

If the result of the determination in step S13 shows that the systolic blood pressure is higher than the threshold TH, the wearable blood pressure monitor 1 returns to step S11. Then, in steps S11 to S13, both the blood pressure measurement process per one heartbeat and the determination process of the measured systolic blood pressure are performed. The blood pressure measurement per one heartbeat and the blood pressure determination process are repeatedly performed in synchronization with the heartbeat. In the blood pressure determination process, the systolic blood pressure for each beat is compared with a systolic blood pressure one beat prior thereto; however, it may be compared with a systolic blood pressure multiple beats (e.g., two or three beats) prior thereto. In short, the cycle of the blood pressure determination may be set for the appropriate number of beats according to the change characteristics of the systolic blood pressure associated with the occurrence of the apneic condition due to sleep apnea syndrome.

On the other hand, let us assume that the result of the determination in step S13 shows that the systolic blood pressure has decreased to the threshold TH or lower. In this case, the wearable blood pressure monitor 1 determines, in step S14 under the control of the warning estimator 12, whether or not the systolic blood pressure measured per one heartbeat is lower than a systolic blood pressure measured at one beat prior thereto. Each time the systolic blood pressure decreases, a count value of the number of continuous decreases is tallied in step S15.

Subsequently, in step S16, the warning estimator 12 determines whether or not the count value of the number of continuous decreases is equal to or greater than a threshold. This threshold is set, for example, to correspond to the time length indicating the decreasing tendency of the systolic blood pressure shown in D of FIG. 7. If the result of the determination shows that the count value does not reach the threshold, the wearable blood pressure monitor 1 returns to step S11 and repeats a series of blood pressure measurement process and determination process in steps S11 to S16.

On the other hand, let us assume that the result of the determination in step S16 shows that the count value has reached the threshold. In this case, the wearable blood pressure monitor 1 generates an activating signal for activating the CPAP apparatus 2 in step S17 under the control of the activating signal transmission controller 13, and transmits the activating signal from the communication unit 51 to the CPAP apparatus 2. At the same time, the activating signal transmission controller 13 stores information indicating the transmission result of the activating signal in the activation history memory 22 in step S18. The information indicating the transmission result of the activating signal includes an identification code indicating the activating signal and data indicating the transmission date and time.

Let us assume that, before the count value of the number of continuous decreases reaches the threshold, it is detected in step S14 that the systolic blood pressure at the most recent heartbeat is higher than the systolic blood pressure immediately therebefore. In this case, the warning estimator 12 does not regard the decrease in the systolic blood pressure as a sign of the blood pressure surge, resets the count value of the number of continuous decreases in step S19, and returns to step S11. The count value of the number of continuous decreases need not be reset simply when the increase in the systolic blood pressure is detected once, but may be reset when the increase in the systolic blood pressure is detected multiple times before the count value reaches the threshold.

Finally, the wearable blood pressure monitor 1 monitors an operation of stopping the sleeping mode in step S20. While the sleeping mode is not released, steps S11 to S19 are repeated, and when the operation of releasing the sleeping mode is detected, the mode is shifted to a normal mode.

(2) Operation of CPAP Apparatus 2

When a power switch (not shown) of the CPAP apparatus 2 is turned on, the power supply voltage Vcc of the battery circuit 400 is supplied to each unit in the apparatus, and the apparatus 2 is temporarily brought into an operating state. However, when the controller 200 detects that the power switch is turned on in step S21, the controller 200 sets the apparatus to a standby mode in step S22 under the control of the drive controller 201. In the standby mode, only the controller 200 and the communication unit 300 are in an operating state, and the air emission unit 100 is set to an operation stop state.

In the standby state, the CPAP apparatus 2 monitors the reception of the activating signal in step S23 while monitoring the operation of turning off the power switch in step S26 under the control of the drive controller 201. When the activating signal transmitted from the wearable blood pressure monitor 1 is received by the communication unit 300, the power supply voltage Vcc is supplied to the air emission unit 100 in step S24 to set the air emission unit 100 to an operating state.

Thus, air is sent into the nasal cavity of the target person 3, whereby the obstruction of the airway is alleviated and the target person 3 returns from the apneic condition to the breathable state. The elimination of the sleep apnea also suppresses the occurrence of a blood pressure surge.

When the air emission unit 100 commences the air supply operation, the CPAP apparatus 2 determines whether or not a preset operation continuation time has elapsed since the start of the air supply in step S25 under the control of the drive controller 201. When the operation continuation time has elapsed, the process returns to step S21, where the operation mode of the apparatus 2 is returned to the standby mode. As a result, the air emission unit 100 stops operating. The operation continuation time is set, for example, according to the maximum length of a single apnea continuation time of the target person 3.

The air supply operation of the air emission unit 100 is repeatedly performed every time the activating signal is received from the wearable blood pressure monitor 1 until the power switch is turned off. When the target person 3, for example, wakes up and turns off the power switch, the drive controller 201 proceeds from step S26 to step S27 and stops the operation of all parts in the apparatus 2.

(Effects)

As detailed above, in the embodiment, the variation of the systolic blood pressure while the target person 3 is sleeping is monitored by the wearable blood pressure monitor 1, and when the systolic blood pressure continuously decreases to the threshold TH or lower for a predetermined time or longer, the variation of the systolic blood pressure is estimated as a sign of a blood pressure surge associated with the onset of sleep apnea syndrome, and the activating signal is output to the CPAP apparatus 2 to commence the air supply operation.

Therefore, it is possible to automatically start the operation of air supply to the target person 3 with the CPAP apparatus 2 before the target person 3 undergoes a blood pressure surge due to the influence of sleep apnea. That is, continuous positive airway pressure with the CPAP apparatus 2 as a measure against sleep apnea syndrome can be timely performed to the target person 3, whereby it is possible to suppress the occurrence of the blood pressure surge associated with the onset of the sleep apnea syndrome.

Since the air supply operation of the CPAP apparatus 2 can be stopped in the period until the sign of the blood pressure surge is estimated, it is possible to reduce the power consumption of the CPAP apparatus 2 as compared to a case where the air supply operation is always performed during sleep. This is extremely effective, particularly in the case of a micropump-type apparatus that uses a battery as a power source, as it becomes difficult to stop the operation during sleep and a large-capacity battery is not needed.

Since the CPAP apparatus 2 is caused to perform the air supply operation only when necessary, and the air supply operation is stopped in other periods, it is possible to suppress the noise of the CPAP apparatus 2 in a period when the continuous positive airway pressure need not be performed by the CPAP apparatus 2 during sleep, and possible to improve the quietness during sleep.

In the embodiment, the blood pressure of the target person 3 is measured per one heartbeat; therefore, it is possible to almost continuously measure the blood pressure variation of the target person 3 and, accordingly, possible to reliably estimate the sign of the blood pressure surge associated with the onset of sleep apnea syndrome without missing the sign.

Other Embodiments (1) In the above embodiment, when the systolic blood pressure decreases to the threshold TH or lower, and the decreasing tendency continues for a certain period of time or longer, as shown in D of FIG. 7 (when the count value of the number of continuous decreases reaches the threshold or higher), a blood pressure variation at this time is estimated as a sign of a blood pressure surge, and the CPAP apparatus 2 is activated. However, the present embodiment is not limited thereto. The CPAP apparatus 2 may be activated by estimating, as a sign of a blood pressure surge, a blood pressure variation when the systolic blood pressure decreases to the threshold TH or lower (as shown in FIG. 7), the decreasing tendency continues for a certain period of time or longer (as shown in D of FIG. 7), thereafter the blood pressure turns upward (as shown in U of FIG. 7), and the increasing tendency continues for a certain period of time or longer. This allows for even more accurate and timely estimation of the sign of the blood pressure surge.

(2) In the above embodiment, the CPAP apparatus 2 is configured to autonomously return to the standby mode at a time point when a preset operation continuation time has elapsed, after the CPAP apparatus 2 starts the air supply operation based on the activating signal output from the wearable blood pressure monitor 1. However, the present embodiment is not limited thereto. For example, the wearable blood pressure monitor 1 may monitor the blood pressure variation of the target person 3 after the activation of the CPAP apparatus 2, and may output, when it is detected that the blood pressure variation continues for a predetermined period in a range near the average value of the nighttime blood pressure, an operation stop signal to the CPAP apparatus 2, thereby stopping the air supply operation of the CPAP apparatus 2. Thereby, even when the period of blood pressure surge occurrence changes, and even when the period of blood pressure surge occurrence differs for each target person, the CPAP apparatus 2 can be continuously operated to supply air during the period of the occurrence.

(3) In the above embodiment, the case where the wearable blood pressure monitor 1 directly transmits the activating signal to the CPAP apparatus 2 has been described as an example. However, the present embodiment is not limited thereto. The activating signal transmitted from the wearable blood pressure monitor 1 may be relayed by a mobile terminal such as a smartphone, or a wireless router, for example, and transmitted to the CPAP apparatus 2.

(4) In the above embodiment, the case where the warning estimator 12 and the activating signal transmission controller 13 are provided in the wearable blood pressure monitor 1 has been described as an example. However, the warning estimator 12 and the activating signal transmission controller 13 may be provided in an information processing terminal such as a smartphone or a tablet terminal, or a server apparatus. In this case, the wearable blood pressure monitor 1 transmits blood pressure data measured under the control of the blood pressure monitoring controller 11 to the information processing terminal or the server apparatus. On the other hand, the information processing terminal or the server apparatus estimates a sign of a blood pressure surge based on the blood pressure data and transmits an activating signal to the CPAP apparatus 2. Thereby, when the functions of the blood pressure measuring apparatus are distributed to the wearable blood pressure monitor and the information processing terminal or the server apparatus, it is possible to reduce the processing load of the wearable blood pressure monitor and suppress the consumption of the battery.

(5) In addition, the functional configuration of the blood pressure measuring apparatus, the process procedure and process content of the warning estimator, the type and configuration of the CPAP apparatus (a mask-type apparatus, other than a micropump-type one, in which a mask and an apparatus body are connected by a tube may be used), the type of signal transmission path between the blood pressure measuring apparatus and the respiration assistance apparatus (a signal cable other than a wireless cable may be used), and the like can be variously modified without departing from the scope of the present embodiments.

In short, the present invention is not limited to the above-described embodiments as they are, and can be, embodied by modifying the constituent elements without departing from the scope of the invention in the implementation stage. In addition, various inventions can be formed by appropriately combining a plurality of constituent elements disclosed in the above embodiments. For example, some constituent elements may be deleted from all the constituent elements shown in each embodiment. Furthermore, the constituent elements of different embodiments may be appropriately combined.

A part or whole of each of the above-described embodiments may be described as in the appendices below, but not limited thereto.

Appendix 1

A blood pressure measuring apparatus for measuring blood pressure of a target person, the blood pressure measuring apparatus including a hardware processor and a memory connected to the hardware processor,
wherein the hardware processor is configured to: measure blood pressure of the target person; monitor variation of the measured blood pressure; estimate the variation of the blood pressure as a sign of a blood pressure increase associated with an onset of sleep apnea syndrome if the blood pressure continuously decreases to a preset threshold or lower for a predetermined time or longer; and output a sign notification signal to outside of the apparatus if the sign is estimated.

Appendix 2

A blood pressure measurement method performed by a blood pressure measuring apparatus that includes at least one hardware processor and memory, the blood pressure measurement method including:
measuring blood pressure of the target person using the at least one hardware processor and memory;
monitoring, by using the at least one hardware processor and memory, variation of blood pressure measured by the blood pressure measurement unit, and estimating the variation of the blood pressure as a sign of a blood pressure increase associated with an onset of sleep apnea syndrome if the blood pressure continuously decreases to a preset threshold or lower for a predetermined time or longer; and
outputting, by using the at least one hardware processor and memory, a sign notification signal to outside of the apparatus if the sign of the blood pressure increase is estimated.

Appendix 3

A respiration assistance apparatus which is connected, via a signal transmission path, to a blood pressure measuring apparatus configured to output an activating signal if a sign of a blood pressure surge is detected from blood pressure variation of a target person, the respiration assistance apparatus including a hardware processor and a memory connected to the hardware processor,
wherein the hardware processor is configured to: receive an activating signal transmitted from the blood pressure measuring apparatus via the signal transmission path; stop an operation for continuous positive airway pressure as a measure against sleep apnea syndrome for the target person in a standby state; and start the operation for the continuous positive airway pressure in response to reception of the activating signal.

REFERENCE SIGNS LIST

1. Wearable blood pressure monitor
2. CPAP apparatus
3. Target person
10. Controller
11. Blood pressure monitoring controller
12. Warning estimator
13. Activating signal transmission controller
20. Memory
21. Blood pressure data memory
22. Activation history memory
30. Blood pressure monitoring unit
31. Blood pressure sensor
32. Air-bag
33. Pump
34. Pump driving circuit
35. Pressure sensor
41. Operating unit
42. Display
51. Communication unit
52. Antenna
61. Motion sensor
62. Environment sensor
71. Battery circuit
72. Battery
100. Air emission unit
101, 102. Emission hole
200. Controller
201. Drive controller
300. Communication unit
301. Antenna
400. Battery circuit
401. Battery

The invention claimed is:

1. A blood pressure monitoring apparatus comprising:
a blood pressure sensor configured to measure blood pressure of a target person;
a warning estimator configured to monitor variation of blood pressure measured by the blood pressure sensor, estimate a sign of a blood pressure increase associated with an onset of obstructive sleep apnea syndrome based on the blood pressure continuously decreasing to a preset threshold or lower for a predetermined time or longer, and determine the onset of obstructive sleep apnea syndrome when the blood pressure reaches the preset threshold or lower for the predetermined time or longer; and
a signal transmitter configured to output a notification signal to a continuous positive airway pressure apparatus when the sign of the blood pressure increase associated with the onset of obstructive sleep apnea syndrome is estimated by the warning estimator; wherein
the signal transmitter is configured to output, as the notification signal, an activating signal to the continuous positive airway pressure apparatus to perform continuous positive airway pressure by sending air to a nasal cavity of the target person as a measure against the obstructive sleep apnea syndrome.

2. The blood pressure monitoring apparatus according to claim 1, wherein the blood pressure sensor is configured to measure blood pressure of the target person per one heartbeat.

3. The blood pressure monitoring apparatus according to claim 1, wherein the warning estimator is configured to estimate the sign of the blood pressure increase accompanying the onset of the obstructive sleep apnea syndrome when the measured blood pressure continuously decreases to the preset threshold or lower for the predetermined time or longer, and starts to increase.

4. A blood pressure monitoring method performed by a blood pressure monitoring apparatus to monitor a blood pressure of a target person, the method comprising:
measuring blood pressure of the target person;
monitoring variation of the blood pressure measured, estimating a sign of a blood pressure increase associated with an onset of obstructive sleep apnea syndrome based on the blood pressure continuously decreasing to a preset threshold or lower for a predetermined time or longer, and determining the onset of obstructive sleep apnea syndrome when the blood pressure reaches the preset threshold or lower for the predetermined time or longer; and
outputting a notification signal to activate a continuous positive airway pressure apparatus when the sign of the blood pressure increase associated with the onset of obstructive sleep apnea syndrome is estimated to perform continuous positive airway pressure by sending air to a nasal cavity of the target person as a measure against the obstructive sleep apnea syndrome.

5. A non-transitory computer readable medium storing a computer program which is executable by a computer to provide the steps of:
measuring blood pressure of a target person;
monitoring variation of the blood pressure measured, estimating a sign of a blood pressure increase associated with an onset of obstructive sleep apnea syndrome based on the blood pressure continuously decreasing to a preset threshold or lower for a predetermined time or longer, and determining the onset of obstructive sleep apnea syndrome when the blood pressure reaches the preset threshold or lower for the predetermined time or longer; and
outputting a notification signal to activate a continuous positive airway pressure apparatus when the sign of the blood pressure increase associated with the onset of obstructive sleep apnea syndrome is estimated to perform continuous positive airway pressure by sending air to a nasal cavity of the target person as a measure against the obstructive sleep apnea syndrome.

* * * * *